United States Patent
Agarkhed et al.

(10) Patent No.: US 11,419,802 B2
(45) Date of Patent: Aug. 23, 2022

(54) EXTRUDED SOAP BAR CONTAINING 12-HYDROXYSTEARIC ACID WITH ENHANCED ANTIMICROBIAL EFFICACY

(71) Applicant: CONOPCO, INC., Trumbull, CT (US)

(72) Inventors: Ajit Manohar Agarkhed, Thane (IN); Nitish Kumar, Bihar (IN); Amitabha Majumdar, Bangalore (IN); Mruthyunjaya Swamy Mathapathi, Bangalore (IN)

(73) Assignee: CONOPCO, INC., Englewood Cliffs, NJ (US)

( * ) Notice: Subject to any disclaimer, the term of this patent is extended or adjusted under 35 U.S.C. 154(b) by 0 days.

(21) Appl. No.: 17/288,582

(22) PCT Filed: Oct. 24, 2019

(86) PCT No.: PCT/EP2019/078981
§ 371 (c)(1),
(2) Date: Apr. 26, 2021

(87) PCT Pub. No.: WO2020/099086
PCT Pub. Date: May 22, 2020

(65) Prior Publication Data
US 2021/0308025 A1    Oct. 7, 2021

(30) Foreign Application Priority Data
Nov. 12, 2018  (EP) .................................... 18205699

(51) Int. Cl.
| | |
|---|---|
| *C11D 9/04* | (2006.01) |
| *A61K 8/365* | (2006.01) |
| *A61K 8/02* | (2006.01) |
| *A61K 8/34* | (2006.01) |
| *A61Q 19/10* | (2006.01) |

(52) U.S. Cl.
CPC ............ *A61K 8/365* (2013.01); *A61K 8/0216* (2013.01); *A61K 8/345* (2013.01); *A61Q 19/10* (2013.01)

(58) Field of Classification Search
CPC . C11D 17/0047; C11D 17/044; C11D 17/006; C11D 13/18; C11D 9/005; C11D 9/007; C11D 9/04; C11D 3/2079; C11D 3/0094; C11D 3/042; C11D 1/04
See application file for complete search history.

(56) References Cited

U.S. PATENT DOCUMENTS

| | | | |
|---|---|---|---|
| 4,260,507 A | 4/1981 | Barrett | |
| 4,767,560 A | 8/1988 | Gervasio | |
| 5,227,086 A | 7/1993 | Kacher et al. | |
| 6,143,704 A | 11/2000 | Van Gunst et al. | |
| 6,458,751 B1 * | 10/2002 | Abbas | C11D 1/04 510/141 |
| 7,776,347 B2 * | 8/2010 | Kerschner | A61K 8/922 424/401 |
| 2002/0137643 A1 * | 9/2002 | Abbas | C11D 10/042 510/141 |
| 2004/0097387 A1 | 5/2004 | Taylor et al. | |
| 2006/0003908 A1 * | 1/2006 | Brennan | C11D 1/28 510/141 |
| 2007/0129272 A1 * | 6/2007 | O'Connor | C11D 17/006 510/141 |
| 2008/0058237 A1 * | 3/2008 | Brennan | A61K 8/466 510/153 |
| 2008/0125340 A1 * | 5/2008 | Dail | A61K 8/416 510/130 |
| 2014/0024573 A1 * | 1/2014 | Agarkhed | C11D 10/042 510/394 |

FOREIGN PATENT DOCUMENTS

| | | |
|---|---|---|
| CN | 1323341 | 11/2001 |
| GB | 2110711 | 6/1983 |
| WO | WO9319154 | 9/1993 |
| WO | WO9503391 | 2/1995 |
| WO | WO0022082 | 4/2000 |
| WO | WO03010273 | 2/2003 |
| WO | WO2006002892 | 1/2006 |
| WO | WO2012136502 | 10/2012 |

OTHER PUBLICATIONS

Search Report and Written Opinion in EP18205699; dated May 8, 2019; European Patent Office (EPO).
Search Report and Written Opinion in PCTEP2019078981; dated Dec. 13, 2019; World Intellectual Property Org. (WIPO).
Written Opinion 2 in PCTEP2019078981; dated Nov. 6, 2020; World Intellectual Property Org. (WIPO).
IPRP2 in PCTEP2019078981; dated Feb. 19, 2021; World Intellectual Property Org. (WIPO).

* cited by examiner

*Primary Examiner* — Charles I Boyer
(74) *Attorney, Agent, or Firm* — Krista A. Kostiew

(57) ABSTRACT

The present invention relates to an extruded soap bar composition. It more particularly relates to a soap bar composition which delivers the enhanced antimicrobial benefit to skin while ensuring that the soap bar is easy to extrude. This is achieved by including free fatty acids in the soap bar composition while ensuring that part of the free fatty acid is hydroxy stearic acid.

5 Claims, No Drawings

EXTRUDED SOAP BAR CONTAINING 12-HYDROXYSTEARIC ACID WITH ENHANCED ANTIMICROBIAL EFFICACY

CROSS REFERENCE TO RELATED APPLICATIONS

The present application is a U.S. National Phase Application under 35 U.S.C. § 371 of International Application No. PCT/EP2019/078981, filed on Oct. 24, 2019, which claims priority to European Patent Application No. 18205699.4, filed on Nov. 12, 2018, the contents of which are incorporated herein in their entireties.

FIELD OF THE INVENTION

The present invention relates to an extruded soap bar composition. It more particularly relates to a soap bar composition which delivers the benefit of enhanced antimicrobial efficacy to skin while ensuring that it is easy to extrude.

BACKGROUND OF THE INVENTION

Surfactants have been used for personal wash applications for a long time. There are many category of products in the personal wash market e.g. body wash, face wash, hand wash, soap bars, shampoos etc. Products which are marketed as body wash, face wash and shampoos are generally in liquid form and are made of synthetic anionic surfactants. They are generally sold in plastic bottles/containers. Soap bars and hand wash products generally contain soaps. Soap bars do not need to be sold in plastic containers and are able to retain their own shape by virtue of being structured in the form of a rigid solid. Soaps bars are usually sold in cartons made of cardboard.

Soap bars are generally prepared through one of two routes. One is called the cast bar route while the other is called the milled and plodded route (also known as extrusion route). The cast bar route has inherently been very amenable in preparing low TFM (total fatty matter) bars. Total fatty matter is a common way of defining the quality of soap. TFM is defined as the total amount of fatty matter, mostly fatty acids, that can be separated from a sample of soap after splitting with a mineral acid, usually hydrochloric acid. In the cast bar soaps, the soap mixture is mixed with polyhydric alcohols and poured in casts and allowed to cool and then the soap bars are removed from the casts. The cast bar route enables production at relatively lower throughput rates.

In the milled and plodded route, the soap is prepared with high water content and then spray dried to reduce the moisture content and to cool the soap after which other ingredients are added and then the soap is extruded through a plodder and optionally cut and stamped to prepare the final soap bar. The milled and plodded soaps generally have a high TFM in the range of 60 to 80 weight percent.

Milled and plodded soap bars are also known as extruded soap bars. They are composed of very many different types of soaps. Most soap compositions comprise both water insoluble as well as water soluble soaps. Their structure is generally characterized by a brick and mortar type structure. Insoluble soaps (called bricks) usually consist of higher chain C16 and C18 soaps (stearate and palmitate soap). They are generally included in soap bars to provide structuring benefits i.e they provide shape to the bars. Soap bars also consist of water soluble soaps (which act as the mortor) which are generally unsaturated C18:1 and 18:2 sodium soap (oleate soap) in combination with short chain fatty acids (generally C8 to C12 or even up to C14 soap). Water soluble soaps generally aid in cleaning.

The present inventors have found that superfatting i.e. inclusion of free fatty acids in the soap composition provides for enhanced antimicrobial activity post use of the soap by ensuring that antimicrobial peptides (AMPs) present on skin are minimally affected. However inclusion of free fatty acids at high amounts (e.g. at about 10%) makes the soap bar difficult to extrude. The present inventors after extensive experimentation, were surprised to note that this problem is solved by including hydroxystearic acid, preferably 12-hydroxystearic acid (12-HSA) as a substantial part of the free fatty acids added.

The newly formulated soap bar compositions are found to exhibit enhanced antimicrobial efficacy to skin while being as convenient to extrude as conventional soap bars. Soap bars superfatted with 12-hydroxystearic acid (12-HSA) have been reported. U.S. Pat. No. 4,260,507 (Lever Brothers, 1981) discloses a personal washing tablet based on tallow soap wherein the lather properties are surprisingly improved by inclusion of up to 40% by weight of active detergent of a defined sulphate/sulphonate synthetic detergent having not more than 10 carbon atoms in a linear chain. In some of the examples 15% of 12-HSA have been included as superfatting to improve lather. This document does not disclose that superfatting, a part of which is 12-HSA (upto a maximum of 10 wt %) helps to improve antimicrobial efficacy while ensuring ease of extrusion.

GB2110711 (Unilever, 1983) discloses soap bars comprising at least 30% by weight tallow scrap and 3-20% by wt of water soluble hydroxystearic acid salts. This patent discloses salt of HSA and not HSA itself and so the soap bar is not related to superfatting at all.

It is thus an object of the present invention to provide for a soap bar composition that provides enhanced antimicrobial efficacy while being easy to extrude.

It is another object of the present invention to provide for a soap bar composition that exhibits enhanced antimicrobial efficacy, is easy to extrude, and also delivers the expected high lather generation from super fatted bars.

SUMMARY OF THE INVENTION

The present invention relates to a soap bar composition comprising
(i) 45 to 85% total amount of soap by weight of the composition;
(ii) 2 to 15% of total free fatty acid by weight of the composition; and
(iii) 14 to 21% of water by weight of the composition
Wherein the free fatty acid includes 0.3 to 10% of hydroxystearic acid by weight of the composition.

DETAILED DESCRIPTION OF THE INVENTION

These and other aspects, features and advantages will become apparent to those of ordinary skill in the art from a reading of the following detailed description and the appended claims. For the avoidance of doubt, any feature of one aspect of the present invention may be utilized in any other aspect of the invention. The word "comprising" is intended to mean "including" but not necessarily "consisting of" or "composed of." In other words, the listed steps or options need not be exhaustive. It is noted that the examples given in the description below are intended to clarify the invention and are not intended to limit the invention to those examples per se. Similarly, all percentages are weight/weight percentages unless otherwise indicated. Except in the operating and comparative examples, or where otherwise explicitly indicated, all numbers in this description and claims indicating amounts of material or conditions of reaction, physical properties of materials and/or use are to be understood as modified by the word "about". Numerical ranges expressed in the format "from x to y" are understood to include x and y. When for a specific feature multiple preferred ranges are described in the format "from x to y", it is understood that all ranges combining the different endpoints are also contemplated.

The present invention relates to a soap bar composition. By a soap bar composition is meant a cleansing composition comprising soap which is in the form of a shaped solid. The soap bar of the present invention comprises 45 to 85% total amount of soap. The term soap means salt of fatty acid. Preferably, the soap is soap of C8 to C24 fatty acids.

The cation may be an alkali metal, alkaline earth metal or ammonium ion, preferably alkali metals. Preferably, the cation is selected from sodium or potassium. The soap may be saturated or unsaturated. Saturated soaps are preferred over unsaturated soaps for stability. The oil or fatty acids may be of vegetable or animal origin.

The soap may be obtained by saponification of oils, fats or fatty acids. The fats or oils generally used to make soap bars may be selected from tallow, tallow stearins, palm oil, palm stearins, soya bean oil, fish oil, castor oil, rice bran oil, sunflower oil, coconut oil, babassu oil, and palm kernel oil. The fatty acids may be from coconut, rice bran, groundnut, tallow, palm, palm kernel, cotton seed or soyabean.

The fatty acid soaps may also be synthetically prepared (e.g. by the oxidation of petroleum or by the hydrogenation of carbon monoxide by the Fischer-Tropsch process). Resin acids, such as those present in tall oil, may also be used. Naphthenic acids may also be used.

The soap bar may additionally comprise synthetic surfactants selected from one or more from the class of anionic, non-ionic, cationic or zwitterionic surfactants, preferably from anionic surfactants. These synthetic surfactants, as per the present invention, are included in less then 8%, preferably less then 4%, more preferably less then 13, further more preferably less than 2%, even further more preferably less than 1% by weight of the composition and optimally absent from the composition.

The composition of the present invention is in the form of a shaped solid for example a bar. The cleaning soap composition is generally a wash off products have sufficient amount of surfactants included therein that it is used for cleansing the desired topical surface e.g. the whole body, the hair and scalp or the face. It is applied on the topical surface and left thereon only for a few seconds or minutes and washed off thereafter with copious amounts of water.

The soap bar of the present invention includes 45 to 85% total soap, preferably 60 to 80% more preferably 65 to 80% soap by weight of the composition. The soap bars of the present invention includes low molecular weight soaps (C8 to C12 soaps) which are generally water soluble, which is in the range of 1 to 40%. It is preferred that the soap bar includes 40 to 80 wt % of the soap of C16 to C22 fatty acid, which are generally water insoluble soaps. A further preferred aspect relates to predominantly water insoluble soaps vis. stearate and palmitate soaps to be included in 40 to 72%. Unsaturated fatty acid soaps may also be included in the total soap content of the composition. Unsaturated soaps are preferably oleic acid soaps.

The soaps bar composition comprises 2 to 15%, preferably 4 to 12% by weight of free fatty acids. By free fatty acids is meant a carboxylic acid comprising a hydrocarbon chain and a terminal carboxyl group.

Suitable fatty acids are C8 to C22 fatty acids. Preferred fatty acids are C12 to C18, preferably predominantly saturated, straight-chain fatty acids. However, some unsaturated fatty acids can also be employed. Of course the free fatty acids can be mixtures of shorter chainlength (e.g., 010 to C14) and longer chainlength (e.g., C16-C18) chain fatty acids. For example, one useful fatty acid is fatty acid derived from high-laurics triglycerides such as coconut oil, palm kernel oil, and babasu oil. The fatty acid can be incorporated directly or they can be generated in-situ by the addition of a protic acid to the soap during processing. Examples of suitable protic acids include: mineral acids such as hydrochloric acid and sulfuric acid, adipic acid, citric acid, glycolic acid, acetic acid, formic acid, fumaric acid, lactic acid, malic acid, maleic acid, succinic acid, tartaric acid, branched fatty acids and polyacrylic acid.

The presence of free fatty acids such as lauric, palmitic, stearic, oleic and others in the soap bar improves the volume and quality of lather, causing it to be more stable with smaller air bubbles which give a lather characterized as richer and creamier, and is also believed to soften skin. Thus, the incorporation of free fatty acids into a soap bar is desirable in that it helps eliminate free alkali, lowers the pH and may make the soap milder. It is also indicated to improve the lathering characteristics of the bar.

It is necessary as per this invention that of the total amount of free fatty acid included in the soap bar composition of the invention, there is included 0.3 to 10% hydroxystearic acid. It is preferred that the hydroxystearic acid is 10-hydroxystearic acid or 12-hydroxystearic acid. Of these, 12-hydroxystearic acid (12-HSA) is more preferred. 12-HSA has the structure as given below:

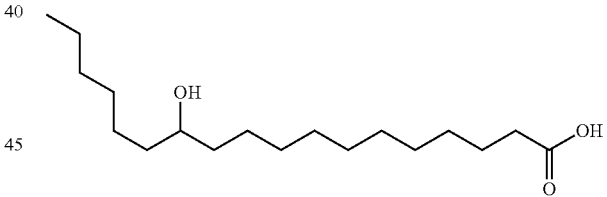

Without wishing to be bound by theory the inventors believe that the inclusion of free fatty acid makes the soap bar soft due to formation of lamellar mortar phase, while the inclusion of part of the free fatty acid with the hydroxystearic acid, preferably 12-HSA overcomes the processing challenge by giving rigidity to the structure due to bonding of hydroxyl group with water and preferably glycerine, if present, thereby enabling convenient extrusion. It has been found that this occurs when the bar has sufficiently high amount of water in the range of 14-21 wt % as compared to certain other conventional bars which have low water content of 10% or less.

The present inventors found that superfatted soap bars with hydroxystearic acid, especially 12-HSA (as per the invention) could be extruded with 4-6% higher water content as compared to conventional superfatted bars which could not be extruded when the water content was increased over 13 to 13.5%. Thus, the soap bar composition of the present invention was found to be much more flexible in terms of inclusion of higher amounts of water which helped save precious raw materials and cost.

The composition preferably comprises a polyhydric alcohol (also called polyol) or mixture of polyols. Polyol is a term used herein to designate a compound having multiple hydroxyl groups (at least two, preferably at least three) which is highly water soluble, preferably freely soluble, in water.

Many types of polyols are available including: relatively low molecular weight short chain polyhydroxy compounds such as glycerol and propylene glycol; sugars such as sorbitol, manitol, sucrose and glucose; modified carbohydrates such as hydrolyzed starch, dextrin and maltodextrin, and polymeric synthetic polyols such as polyalkylene glycols, for example polyoxyethylene glycol (PEG) and polyoxypropylene glycol (PPG). Especially preferred polyol are glycerol, sorbitol and their mixtures. Most preferred polyol is glycerol.

In a preferred embodiment, the bars of the invention comprise 0 to 8%, preferably 1 to 7.5% by wt. polyol.

The soap bar composition generally comprises electrolyte and water. Electrolytes as per this invention includes compounds that substantially dissociate into ions in water. Electrolytes as per this invention do not include an ionic surfactant. Suitable electrolytes for inclusion in the soap making process are sodium sulfate, sodium chloride, sodium acetate, sodium citrate, potassium chloride, potassium sulfate, sodium carbonate and other mono or di or tri salts of alkaline earth metals, more preferred electrolytes are sodium chloride, sodium sulfate, sodium citrate, potassium chloride and especially preferred electrolyte is sodium chloride. For the avoidance of doubt, it is clarified that the electrolyte is a non-soap material. Electrolyte is preferably included in 0.5 to 5%, preferably 0.5 to 3%, further more preferably 1 to 3% by weight of the composition. Water is used as the slurrying medium for the soap and is preferably included in 16 to 22% by weight of the composition.

The soap composition may be made into a bar by a process that including extruding the mixture in a conventional plodder. The plodded mass may then be optionally cut to a desired size and stamped with a desirable indicia. Another additional benefit of the present invention is that the soap bar compositions thus prepared by extrusion are also found to be easy to stamp with a desirable indicia. Soap bars with high levels of superfatting and without 12-HSA were found to be sticky and difficult to stamp.

The various ingredients that make up the final soap bar composition are as described below:

Organic and Inorganic Adjuvant Materials

The total level of the adjuvant materials used in the bar composition should be in an amount not higher than 50%, preferably 1 to 50%, more preferably 3 to 45% by wt. of the soap bar composition.

Suitable starchy materials which may be used include natural starch (from corn, wheat, rice, potato, tapioca and the like), pregelatinzed starch, various physically and chemically modified starch and mixtures thereof. By the term natural starch is meant starch which has not been subjected to chemical or physical modification—also known as raw or native starch.

A preferred starch is natural or native starch from maize (corn), cassava, wheat, potato, rice and other natural sources of it. Raw starch with different ratio of amylose and amylopectin: e.g. maize (25% amylose); waxy maize (0%); high amylose maize (70%); potato (23%); rice (16%); sago (27%); cassava (18%); wheat (30%) and others. The raw starch can be used directly or modified during the process of making the bar composition such that the starch becomes gelatinized, either partially or fully gelatinized.

Another suitable starch is pre-gelatinized which is starch that has been gelatinized before it is added as an ingredient in the present bar compositions. Various forms are available that will gel at different temperatures, e.g., cold water dispersible starch. One suitable commercial pre-gelatinized starch is supplied by National Starch Co. (Brazil) under the trade name FARMAL® CS 3400 but other commercially available materials having similar characteristics are suitable.

The adjuvant system may optionally include insoluble particles comprising one or a combination of materials. By insoluble particles is meant materials that are present in solid particulate form and suitable for personal washing. Preferably, there are mineral (e.g., inorganic) or organic particles.

The insoluble particles should not be perceived as scratchy or granular and thus should have a particle size less than 300 microns, more preferably less than 100 microns and most preferably less than 50 microns.

Preferred inorganic particulate material includes talc and calcium carbonate. Talc is a magnesium silicate mineral material, with a sheet silicate structure and a composition of $Mg_3Si_4(OH)_{22}$, and may be available in the hydrated form. It has a plate-like morphology, and is essentially oleophilic/hydrophobic, i.e., it is wetted by oil rather than water.

Calcium carbonate or chalk exists in three crystal forms: calcite, aragonite and vaterite. The natural morphology of calcite is rhombohedral or cuboidal, acicular or dendritic for aragonite and spheroidal for vaterite.

Commercially, calcium carbonate or chalk known as precipitated calcium carbonate is produced by a carbonation method in which carbon dioxide gas is bubbled through an aqueous suspension of calcium hydroxide. In this process the crystal type of calcium carbonate is calcite or a mixture of calcite and aragonite.

Examples of other optional insoluble inorganic particulate materials include alumino silicates, aluminates, silicates, phosphates, insoluble sulfates, borates and clays (e.g., kaolin, china clay) and their combinations.

Organic particulate materials include: insoluble polysaccharides such as highly crosslinked or insolubilized starch (e.g., by reaction with a hydrophobe such as octyl succinate) and cellulose; synthetic polymers such as various polymer lattices and suspension polymers; insoluble soaps and mixtures thereof.

Bar compositions preferably comprise 0.1 to 25% by wt. of bar composition, preferably 5 to 15 by wt. of these mineral or organic particles.

An opacifier may be optionally present in the personal care composition. When opacifiers are present, the cleansing bar is generally opaque. Examples of opacifiers include titanium dioxide, zinc oxide and the like. A particularly preferred opacifier that can be employed when an opaque soap composition is desired is ethylene glycol mono- or di-stearate, for example in the form of a 20% solution in sodium lauryl ether sulphate. An alternative opacifying agent is zinc stearate.

The product can take the form of a water-clear, i.e. transparent soap, in which case it will not contain an opacifier, or alternatively, it can take the form of an opaque liquid soap containing an opacifier such as that herein defined.

The pH of preferred soaps bars of the invention is from 8 to 11, more preferably 9 to 11.

A preferred bar may additionally include up to 30 wt % benefit agents. Preferred benefit agents include moisturizers, emollients, sunscreens and anti-ageing compounds. The agents may be added at an appropriate step during the process of making the bars. Some benefit agents may be introduced as macro domains.

Other optional ingredients like anti-oxidants, perfumes, polymers, chelating agents, colourants, deodorants, dyes, emollients, moisturizers, enzymes, foam boosters, germicides, additional anti-microbials, lathering agents, pearlescers, skin conditioners, stabilisers, superfatting agents, sunscreens may be added in suitable amounts in the process of the invention. Preferably, the ingredients are added after the saponification step. Sodium metabisulphite, ethylene diamine tetra acetic acid (EDTA), borax or ethylene hydroxy diphosphonic acid (EHDP) are preferably added to the formulation.

Another aspect of the present invention relates to a method of providing enhanced antimicrobial efficacy to skin comprising the steps of applying the composition as claimed in any one of the preceding claims on to the desired skin surface followed by rinsing the applied skin surface with water.

The invention will now be illustrated by means of the following non-limiting examples.

EXAMPLES

Example A and 1

Effect of Inclusion of 12-HSA in Superfatted Soap Bars

The following two soap bar compositions as shown in Table-1 were prepared. Example A is a superfatted soap bar without 12-HSA while Example 1 is a superfatted soap bar with similar amount of total superfatting but including about 4% 12-HSA.

TABLE 1

| Ingredient (wt %) | Example A | Example 1 |
|---|---|---|
| Sodium laurate | 2.5 | 4.8 |
| Sodium C16-18 soap | 39.0 | 34.3 |
| Sodium oleate soap | 20.1 | 18.7 |
| Glycerine | 4.0 | 4.1 |
| Sodium chloride | 0.7 | 0.7 |
| Sodium citrate dihydrate | 1.9 | 1.8 |
| Petrolatum | 0.5 | 0.8 |
| Lauric acid | 1.0 | 0.5 |
| Palmitic acid/stearic acid (55:45) | 8.5 | 5.0 |
| 12-HSA | 0.0 | 4.1 |
| Talc | 6.0 | 6.0 |
| Titanium dioxide | 0.5 | 0.5 |
| Minors (perfume, preservative etc) | 0.9 | 2.8 |
| Water | 14.4 | 15.9 |

In the above compositions petrolatum, lauric acid, palmitic/stearic acid and 12-HSA are free fatty acids. The above two compositions were tested for antimicrobial kill of *E. coli* after washing skin with the above soap composition using the following procedure of washing and using the procedure given below for measuring *E. coli* kill.

Prewash step (7 days): A non-antimicrobial soap was given to each volunteer to use for bathing, washing hands, washing forearms etc. Volunteers were instructed to refrain from use of any leave on products (sun screen, hand sanitizer, skin moisturizers, lotion, cream, oil and antimicrobial products) till completion of the study.

On day 8, volunteers were divided in to two groups (group 1 and 2). Each group had 5 volunteers.

Placebo soap bar (Example A) was given to each volunteer of Group-1 and they were asked to use the bar for bathing and washing hands for two weeks. Volunteers were asked to wash the forearm at least twice a day, once during bathing and second during the evening. Similarly, group-2 volunteers were given the test product (Example-1) for two weeks use. The volunteers in this group too were asked to wash forearm at least twice a day, once during bath and second during the evening.

After two weeks (day 15), volunteers were asked to come to study site for analysis. On day 15, volunteers forearm will be washed with respective soap bar by study person using below protocol The soap bar was dipped for 10 seconds in water. Each forearm was wetted with water (100 ml±10 ml). The soap bar was rubbed 10 times back and forth across the length of the forearm. 3 ml±1 ml of water was added on the forearm and it was lathered for 30 seconds. The lather was retained on the forearm for 20 seconds. The forearm was washed with water for 1 minute while making sure that the soap is washed off completely. The excess water was removed by patting dry using sterile tissue paper.

Volunteers were asked to wait at study site for 5 hours. After 5 hours, 10 μl of *E. coli* (10536) from $10^8$ stock was applied on defined circular area on forearm skin (7 cm² circle) for 5 mins. ($10^8$ culture stock was prepared in 10 mM sodium phosphate buffer using 18 to 20 hour old broth culture. The OD was adjusted to 0.8 at 620 nm to attain $10^8$ counts) After 5 mins contact time of *E. coli* on forearm skin, it was recovered by cup scrub method (ASTM method, E2752-10) using 1.5 ml of extraction buffer.

Then each sample was serially diluted in 9 ml of D/E (Dey Engley neutralizing broth) and respective dilutions were plated on MacConkey agar media.

Plates were incubated at 37° C. for 24 h to grow *E. coli* and then colonies were counted and calculated the log cfu/ml by using standard microbiology method.

The data on *E. coli* kill is shown in the Table-2 below:

TABLE 2

| Soap bar | Day 1 (30 min after wash) log reduction | Day 15 (5 hours after wash) log reduction |
|---|---|---|
| Example A | 0.4 | 0.6 |
| Example 1 | 0.5 | 0.6 |

The processability of the soap bars in an extruder as prepared above is summarized below.

| Soap bar | Extrudability | Stampability |
|---|---|---|
| Example A | Was soft and not extrudable | Not easily stampable |
| Example 1 | Extrudable | Stampable |

The data in Table-1 and 2 above indicates that composition as per the invention (Example-1) and a conventional superfatted soap bar (Example A) containing similar levels of free fatty acids give very good antimicrobial efficacy with similar level of kill. However, soap bar as per the invention (Example-1) could be easily extruded and stamped as compared to a conventional superfatted bar (Example-A) where such processing step were difficult to carry out.

Example B, 1

Processibility of Superfatted Bars With and Without 12-HSA

Another composition (Example-B) similar to Example-1 but without 12-HSA was also prepared and the processability of the two soap bar samples was compared. The compositions are shown in Table-3 below:

TABLE 3

| Ingredient (wt %) | Example B | Example 1 |
| --- | --- | --- |
| Sodium laurate | 4.8 | 4.8 |
| Sodium C16-18 soap | 34.3 | 34.3 |
| Sodium oleate soap | 18.7 | 18.7 |
| Glycerine | 4.1 | 4.1 |
| Sodium chloride | 0.7 | 0.7 |
| Sodium citrate dihydrate | 1.8 | 1.8 |
| Petrolatum | 0.5 | 0.8 |
| Lauric acid | 0.5 | 0.5 |
| Palmitic acid/stearic acid (55:45) | 9.0 | 5.0 |
| 12-HSA | 0.0 | 4.1 |
| Talc | 6.0 | 6.0 |
| Titanium dioxide | 0.5 | 0.5 |
| Minors (perfume, preservative etc) | 2.8 | 2.8 |
| Water | 16.3 | 15.9 |

The processability of the soap bars in an extruder as prepared above is summarized below.

TABLE 4

| Soap bar | Extrudability | Stampability |
| --- | --- | --- |
| Example B | Was soft and not extrudable | Not easily stampable |
| Example 1 | Extrudable | Stampable |

The data in Table-3 and 4 above indicates that composition as per the invention (Example-1) could be easily extruded and stamped. On the other hand, a similar soap bar without 12-HSA (Example-B) with similar amount of superfatting was difficult to process.

Examples C,D,2

Effect of the Composition of the Invention (Example 2) on Lather Volume as Compared to Conventional Soap Bars (Examples C and D)

Soap bar compostions as shown in Table-5 were prepared. The soap bar samples were measured for lather volume using the following method.

Lather is generated by trained technicians using a standardised method. The lather is collected and its volume measured.

(i) Tablet Pre-treatment: Wearing a surgeon's glove previously washed in plain soap, all test tablets are washed down at least 10 minutes before starting the test sequence. This is best done by twisting them about 20 times through 180° under running water.

(ii) About 5 litres of water of known hardness and at a specified temperature is taken in a bowl. The water is changed after each bar of soap has been tested.

(iii) The tablet is taken, dipped in the water and then removed. The tablet is twisted 15 times, between the hands, through 180°. The tablet is then placed on the soap dish.

(iv) Lather is generated by the soap remaining on the gloves.

Step 1: This is done by rubbing one hand over the other hand (two hands on same direction) 10 times in the same way.

Step 2: The right hand is then gripped with the left, or vice versa, and the lather is forced to the tips of the fingers. This operation is repeated five times. The above two steps are then repeated. The lather is then placed in the beaker.

(v) The whole procedure of lather generation from paragraph iii is repeated twice more, combining all the lather in the beaker.

(vi) The combined lather is then stirred gently to release large pockets of air. The volume is then read and recorded.

Data analysis is carried out by two way analysis of variance, followed by Turkey's Test.

The lather volume generated by each of the samples is given in Table-5 below:

TABLE 5

| Example Ingredients | C wt % | D wt % | 2 wt % |
| --- | --- | --- | --- |
| Sodium Laurate | 8.2 | 12.4 | 5.1 |
| Sodium Palmate | 60.0 | 65.0 | 55.0 |
| Glycerine | 6.0 | 2.0 | 4.1 |
| sodium chloride | 0.7 | 0.7 | 0.7 |
| Na4EDTA | 0.04 | 0.04 | 0.04 |
| Na4-Etidronate | 0.14 | 0.14 | 0.14 |
| Talc | 6.0 | 2.5 | 6.0 |
| Fatty acid (C12-18) | 0.25 | 0.25 | 5.5 |
| 12-Hydroxystearic acid | 0 | 0 | 4.1 |
| Sodium Citrate dihydrate | 0 | 0 | 1.8 |
| Synthetic surfactants* | 1.0 | 0 | 1.8 |
| Minor ingredients | 2.0 | 2.0 | 2.0 |
| Water | To 100 | To 100 | To 100 |
| Lather Volume (ml) | 216 | 247 | 294 |

*The Synthetic surfactants used was a mixture of alpha olefin sulphonate (AOS), primarily alkyl sulphate (PAS) and coco amido propyl betaine (CAPB).

The data in Table-5 above indicates that the composition as per the invention (Example 2) delivers better lather as compared to the conventional compositions (Examples C and D) without superfatting or 12-HSA

The invention claimed is:

1. A soap bar composition comprising:
   (i) 45 to 85% total amount of soap by weight of the composition;
   (ii) 2 to 15% of total free fatty acid by weight of the composition;
   (iii) 0.5 to 8% polyhydric alcohol; and
   (iv) 14 to 21% water by weight of the composition,
   wherein the free fatty acid includes 12-hydroxystearic acid, wherein the 12-hydroxystearic acid is present in an amount of 0.3 to 10% by weight of the composition.

2. A method of providing enhanced antimicrobial efficacy to skin comprising the steps of applying the composition as claimed in claim 1 on to the desired skin surface followed by rinsing the applied skin surface with water.

3. The composition as claimed in claim 1, wherein the polyhydric alcohol is glycerol.

4. The composition as claimed in claim 1, wherein the composition provides an antimicrobial benefit.

5. The composition as claimed in claim 1, wherein the soap bar composition is formed into a bar via extrusion.

* * * * *